(12) United States Patent
Shetty

(10) Patent No.: US 7,717,872 B2
(45) Date of Patent: May 18, 2010

(54) FLUID SHUNTING APPARATUS AND METHODS

(76) Inventor: Rajesh Kumar Shetty, 9130 Spindletree Way, Jacksonville, FL (US) 32256

( * ) Notice: Subject to any disclaimer, the term of this patent is extended or adjusted under 35 U.S.C. 154(b) by 749 days.

(21) Appl. No.: 11/528,020

(22) Filed: Sep. 27, 2006

(65) Prior Publication Data
US 2007/0093740 A1   Apr. 26, 2007

Related U.S. Application Data

(60) Provisional application No. 60/721,304, filed on Sep. 28, 2005.

(51) Int. Cl.
*A61M 5/00* (2006.01)
(52) U.S. Cl. .................. 604/9; 604/8; 604/264
(58) Field of Classification Search ............ 604/8, 604/9, 264
See application file for complete search history.

(56) References Cited

U.S. PATENT DOCUMENTS

| | | | | |
|---|---|---|---|---|
| 5,171,213 A * | 12/1992 | Price, Jr. | ........................ | 604/9 |
| 6,203,513 B1 * | 3/2001 | Yaron et al. | ..................... | 604/9 |
| 6,589,203 B1 * | 7/2003 | Mitrev | .......................... | 604/27 |
| 6,730,056 B1 * | 5/2004 | Ghaem et al. | .................. | 604/9 |
| 2004/0073156 A1 * | 4/2004 | Brown | ........................... | 604/8 |

* cited by examiner

*Primary Examiner*—Leslie R Deak

(57) ABSTRACT

An implantable fluid shunting apparatus having a tube and a shunt tip attached to the tube end, that tapers towards the end of the shunt tip, a tip lumen extending through the shunt tip in fluid communication with the tube lumen, wherein the tip lumen has a closed end, and has a wall that comprises laser-ablatable material such that an opening can be formed through the wall and into the tip lumen using laser energy on an outer surface of the shunt tip. The shunt tip may consist essentially of the laser-ablatable material; the tube end is attached to an implantable diffusion chamber and the laser-ablatable material may be polypropylene. The tube and the shunt tip may be a one-piece completely integral unit or may be of separate bodies fitted together frictionally adhesively, thermally or chemically welded to the tube.

14 Claims, 3 Drawing Sheets

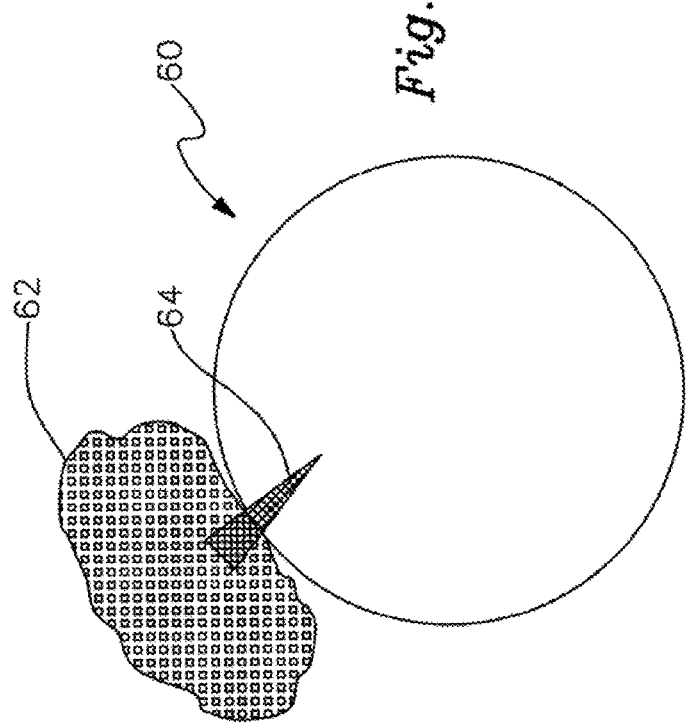
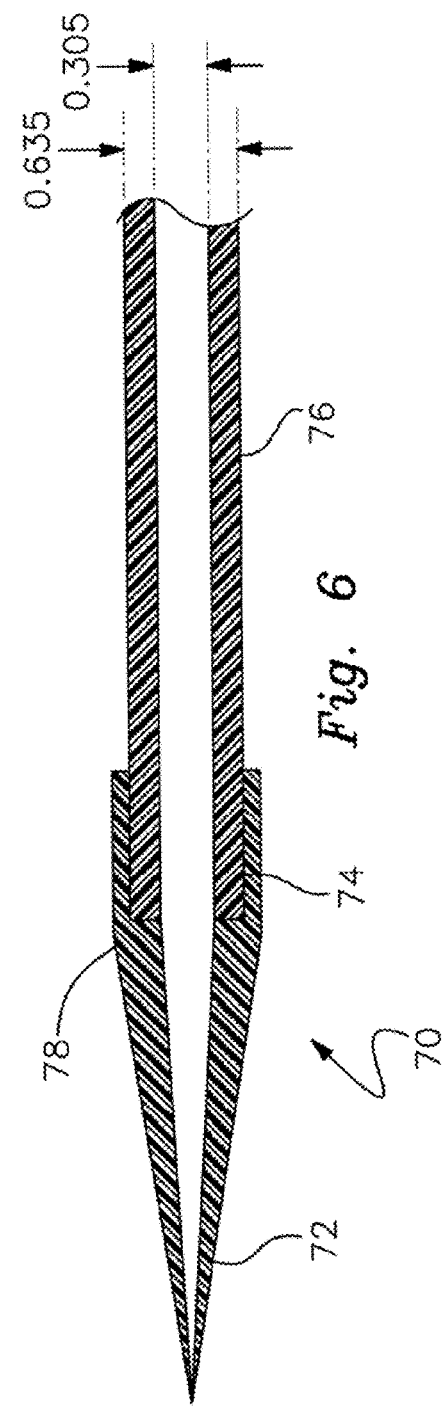

FLUID SHUNTING APPARATUS AND METHODS

CROSS REFERENCE TO RELATED APPLICATIONS

The present application is related to the following U.S. patent application: provisional patent application No. 60/721,304 titled FLUID SHUNTING APPARATUS AND METHODS filed Sep. 28, 2005 which is hereby incorporated by reference as if fully set forth herein.

STATEMENT REGARDING FEDERALLY SPONSORED RESEARCH OR DEVELOPMENT

Not applicable

BACKGROUND OF THE INVENTION

The present invention generally relates to medical devices, and more particularly to devices, apparatus and methods for draining fluid from an eye or other internal body location.

Patients suffering from conditions such as glaucoma may be treated by reduction of the fluid pressure within the eye (or intraocular pressure) to protect the function of the optic nerve. In cases resistant to medication and laser surgery, a variety of surgical techniques and devices may be used to drain fluid from the eye to reduce intraocular pressure (IOP). Examples of some such devices are described in, U.S. Pat. No. 6,881,397 (Nigam) as well as in U.S. Patent Application Publication Nos. US 2005/0119601 A9 (Lynch et al) and US 2005/0192527 A1 (Gharib et al.).

The conventional devices and/or methods typically provide a fistula within the eye that allows fluid to exit the eye to reduce the fluid pressure within the eye. The fluid can then be reabsorbed by the vasculature around the eye. To reduce the risk of low IOP or hypotony, some of the devices may include pressure-based valves or other structures to limit fluid outflow through the device. Conventional shunts, for example, may be provided with suture material located within the lumen of a tube shunt to reduce flow therethrough. In other instances, the tubes may be tied off with sutures to limit flow.

The present invention provides apparatus and methods for controllably draining fluid from an internal body location (such as an eye) by locating the device in or near the internal body location (e.g., the eye) and forming one or more openings in the device after its insertion. Preferably, the size and/or number of the openings can be selected to offer control over the rate at which fluid exits the eye. That control may preferably offer some corresponding control over hypotony.

It is an advantage of the present invention to provide a modifiable shunt tube tip for controllable flow of fluid from the eye.

It is another advantage of the present invention to provide an insertable tube tip that can act as a stand-alone fistula or seton.

It is yet another advantage of the present invention to provide method for insertion of a shunt tube tip into the anterior chamber of the eye.

It is still yet another advantage of the present invention to provide a laser configurable shunt tube tip.

It is another advantage of the present invention to provide a shunt tube tip of varying dimensions and configurations to control fluid flow.

BRIEF SUMMARY OF THE INVENTION

In accordance with a preferred embodiment of the invention, there is disclosed an implantable fluid shunting apparatus having a tube comprising a proximal tube end, a distal tube end, and a tube lumen extending from the proximal tube end to the distal tube end, a shunt tip attached to the distal tube end, wherein a longitudinal axis extends between the distal tube end and a distal tip end, and wherein at least a portion of the shunt tip tapers when moving from the distal tube end towards the distal tip end of the shunt tip, a tip lumen extending through the shunt tip along the longitudinal axis, the tip lumen in fluid communication with the tube lumen, wherein at least a portion of the tip lumen tapers when moving from the distal tube end towards the distal tip end, and wherein the tip lumen comprises a closed end proximate the distal end of the shunt tip, wherein the tip lumen is defined by a wall that comprises laser-ablatable material such that an opening can be formed through the wall and into the tip lumen using laser energy incident on an outer surface of the shunt tip.

In accordance with another preferred embodiment of the invention, there is disclosed an implantable fluid shunting apparatus having a shunt tip comprising a proximal end and a distal end, wherein a longitudinal axis extends between the proximal end and the distal end, and wherein at least a portion of the shunt tip tapers when moving from the proximal end towards the distal end, a tip lumen extending through the shunt tip along the longitudinal axis, the tip lumen comprising an opening at the proximal end of the shunt tip, wherein at least a portion of the tip lumen tapers when moving from the distal tube end towards the distal end, and wherein the tip lumen comprises a closed end proximate the distal end of the shunt tip, wherein the tip lumen is defined by a wail that comprises laser-ablatable material such that an opening can be formed through the wall and into the tip lumen using laser energy incident on an outer surface of the shunt tip.

In accordance with another preferred embodiment of the invention, there is disclosed a method of providing an implantable shunt to drain fluid from an eye having the steps of implanting a portion of a shunt apparatus within the eye of a subject, wherein the shunt apparatus has a tube comprising a proximal tube end, a distal tube end, and a tube lumen extending from the proximal tube end to the distal tube end, a shunt tip attached to the distal tube end, wherein a longitudinal axis extends between the distal tube end and a distal tip end of the shunt tip, and wherein at least a portion of the shunt tip tapers when moving from the distal tube end towards the distal tip end, a tip lumen extending through the shunt tip along the longitudinal axis, the tip lumen in fluid communication with the tube lumen, wherein at least a portion of the tip lumen tapers when moving from the distal tube end towards the distal tip end, and wherein the tip lumen comprises a closed end proximate the distal end of the shunt tip, forming an opening in the shunt tip after implanting the shunt tip in the eye, wherein fluid within the eye is capable of flowing through the tip lumen and into the tube lumen, wherein the opening is formed by ablating a portion of the shunt tip using laser energy.

Other advantages of the present invention will become apparent from the following descriptions, taken in connection with the accompanying drawings, wherein, by way of illustration and example, embodiments of the present invention are disclosed.

BRIEF DESCRIPTION OF THE SEVERAL DRAWINGS

FIG. 5 shows schematic diagram of a preferred embodiment of the invention with a tube shunt placed directly into the anterior chamber of the eye.

FIG. 6 shows a schematic diagram of a tube shunt tip placed on a tube shunt according to a preferred embodiment.

DETAILED DESCRIPTION OF THE PREFERRED EMBODIMENTS

Detailed descriptions of the preferred embodiments are provided herein. It is to be understood, however, that the present invention may be embodied in various forms. Various aspects of the invention may be inverted, or changed in reference to specific part shape and detail, part location, or part composition. Therefore, specific details disclosed herein are not to be interpreted as limiting, but rather as a basis for the claims and as a representative basis for teaching one skilled in the art to employ the present invention in virtually any appropriately detailed system, structure or manner.

Although described herein with respect to implantation within an eye and draining of fluid from an eye, it should be understood that the apparatus and methods of the present invention may find use in other internal body locations where control over fluid flow after implantation of a device is desired. As a result, although in the opthalmological field the terms proximal and 'distal' are used to describe spatial relationships relative to the anterior chamber or interior of the eye, those terms are used herein in the opposite, but more generic, sense in that a distal object is located closer to the interior eye (and farther from, e.g., a practitioner using the object) while a proximal object is located farther from the interior of the eye (and closer to, e.g., a practitioner using the object).

Figure 1:
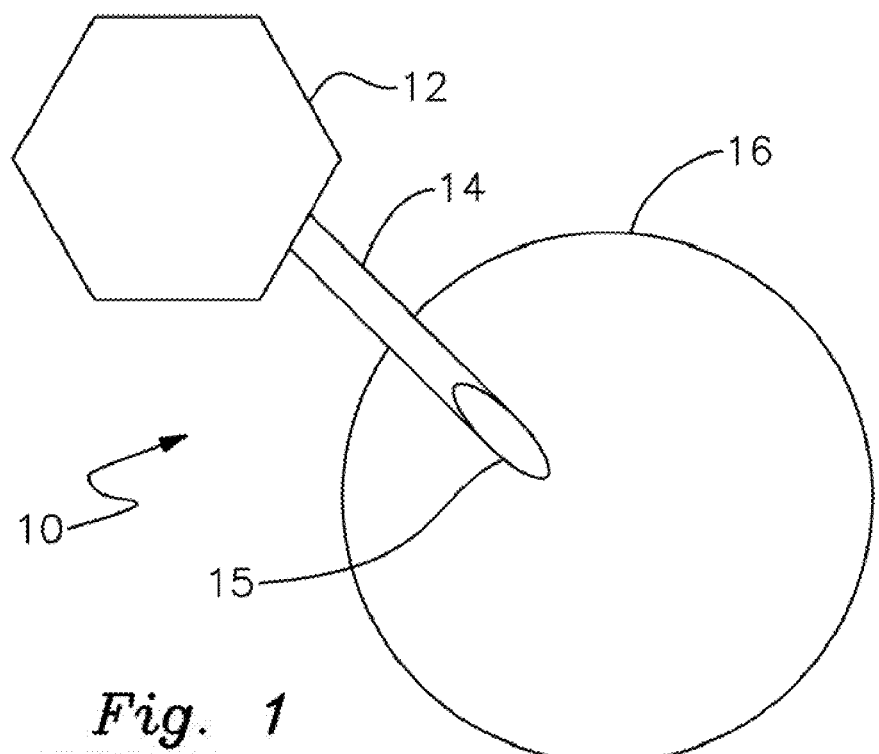
FIG. 1 shows a schematic diagram of a conventional glaucoma tube shunt.

Turning now to FIG. 1, there is shown a schematic diagram of a prior art system for placement of a tube shunt into the eye. Tube shunt system 10 is composed of a tube shunt 14 attached to an implantable diffusion chamber 12 that is inserted into the anterior chamber 16. Diffusion chamber 12 may be of any a variety of shapes and dimensions and is shown here as a hexagon for illustrative purposes only. In this conventional method, the practitioner typically provides a fistula within the eye that allows fluid to exit the eye to reduce the fluid pressure within the eye. The fistula is often cut at the tip in bevel 15 to facilitate entry into the eye. The fluid can then be reabsorbed by the vasculature around the eye.

Figure 2:
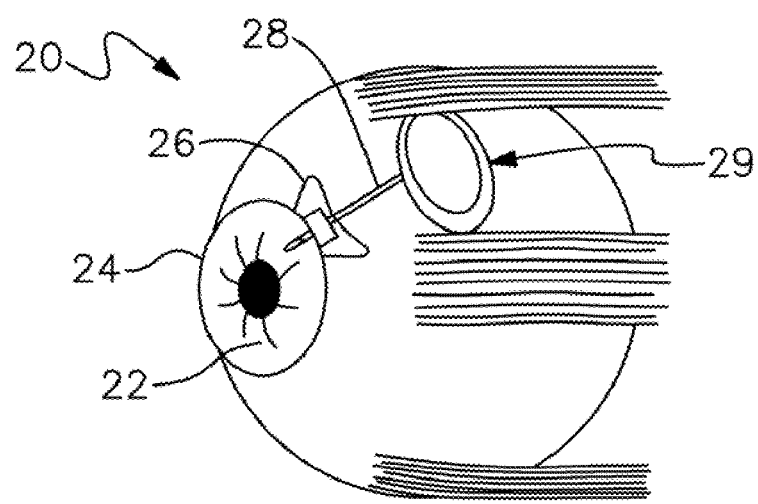
FIG. 2 shows a schematic diagram of an eyeball with a conventional method for insertion of a tube shunt and diffusion chamber about the anterior chamber of the eye.

FIG. 2 shows a typical glaucoma tube shunt implantation into eye 20. Tube shunt 28 and diffusion chamber 29 make up a standard tube shunt assembly. Diffusion chamber 29 is placed under the skin behind the anterior chamber and tube shunt 28 is placed into the anterior chamber below cornea 24 to relieve fluid pressure. Fluid is relieved through tube shunt 28 into diffusion chamber 29 also referred to as a reservoir. In certain cases, bleb 26 is created with a scleral flap to relieve and control intraocular pressure. To reduce the risk of low IOP or hypotony, some of the devices include pressure-based valves or other structures to limit fluid outflow through the device.

Figure 3:
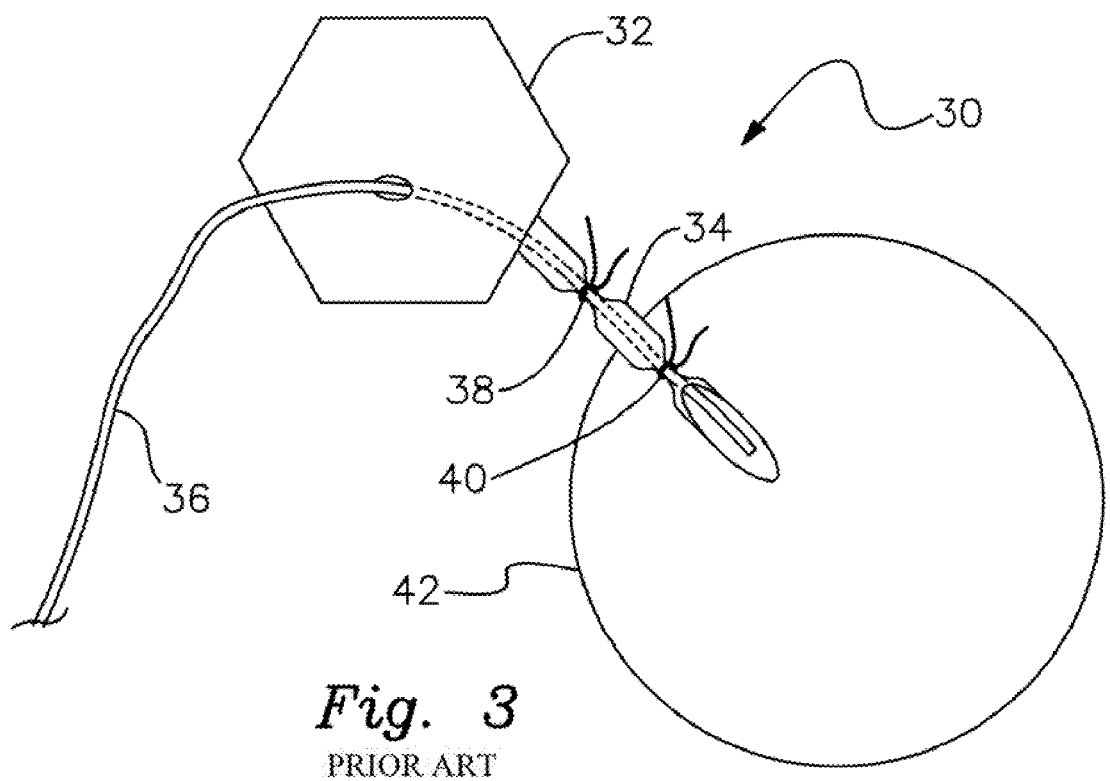
FIG. 3 shows a schematic diagram of a tube shunt and various conventional methods for impeding or stopping flow through the tube.

FIG. 3 shows an alternative prior art method for the control of fluid flow. Tube shunt reservoir 32 and tube shunt 34 are placed conventionally into anterior chamber 42. An internal suture 36 is inserted into the lumen of tube 34 before placement into the eye to create a mechanical blockage thereby slowing down the flow of fluid. One such method is the use of a 4-0 nylon suture that can be removed in the postoperative period. Another method to control fluid flow is the placement of one or more sutures about tube shunt 34 as shown as suture 38 or suture 40. By constricting tube shunt 34 with such sutures, fluid flow is impeded and thus controlled. Typical sutures used may be 6-0 prolene or 8-0 vicryl. None of the prior art or conventional methods permit modifiable fluid flow control by the practitioner and lack the ability to fine tune the fluid flow that is often necessary to achieve desired results.

Figure 4:
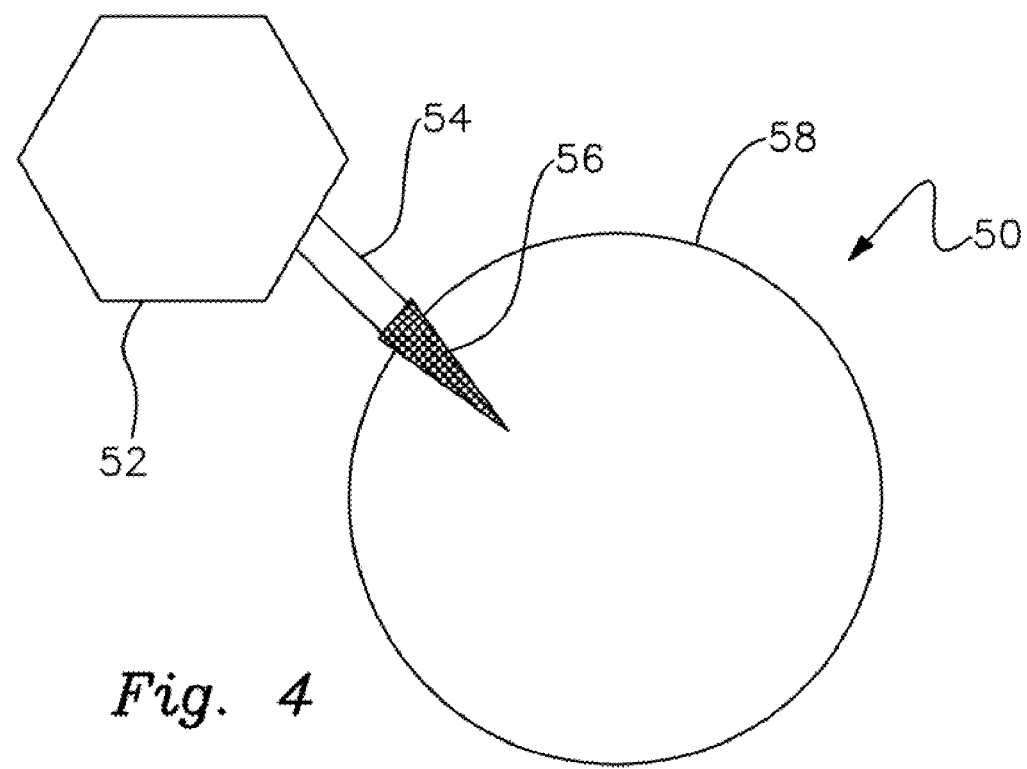
FIG. 4 shows a schematic diagram of a preferred embodiment of the invention with a tube shunt tip placed about the tube shunt.

FIG. 4 is shows a tube shunt tip according to a preferred embodiment of the invention. Reservoir 52 and tube shunt 54 are equipped with shunt tip 56 for restriction of flow into the drainage reservoir. Tube shunt 54 has distal and proximal tube ends with a tube lumen extending from the proximal tube end to the distal tube end. Shunt tip 56 is attached to the distal tube end along the longitudinal axis of tube shunt 54.

The outer shape of shunt tips of the present invention may preferably be tapered when moving from the distal tube end towards the distal tip end of the shunt tips such that their insertion into the eye or other location may be facilitated. As shown in FIG. 4, the shape is conical with a sharp point for piercing surface 58 of anterior chamber 50. The tapered shape may be in the form of a circular cone as shown, although other tapered shapes may also be used, e.g., pyramids (with a variety of polygonal bases), cones with oval bases, etc. The shunt tips of the present invention preferably include a tip lumen extending along their length which is in fluid communication with the tube lumen and where the tip lumen has a closed end proximate the distal end of the shunt tip. Shunt tip 56 is preferably placed over tube 54 at a point that fully covers tube 54 so that only shunt tip 56 intrudes the anterior chamber. In other applications, it may be preferable to insert shunt tip 56 completely inside anterior chamber 50 without departing from the invention. The tip lumen may have a constant cross-sectional area along its length. Alternatively, the cross-sectional size of the tip lumen may change along its length. For example, the cross-sectional size of the tip lumen itself may also be tapered in profile in a manner similar to the outer shape of the tip. As the distal end of the shunt tip is removed, the size of the opening into the tip lumen may increase to provide different flow characteristics based on the size of the opening.

Openings in the shunt tips of the present invention may be laser-ablatable, preferably by directing laser energy at the outer surface of the shunt tip after implantation. As a result, when used in connection with an eye, the laser energy passes through portions of the eye (e.g., a clear cornea) and the fluid located therein before reaching the shunt tip. The shunt tip itself may preferably be manufactured of material that is susceptible to ablation by the laser energy (while producing limited or no debris). The material is also preferably biocompatible such that it is appropriate for implantation within, e.g., the eye of a patient. Examples of suitable materials may include, e.g. polygalactin, polypropylene. etc.

The openings in the shunt tip may be formed in a variety of locations. In some instances, the distal end of the shunt tip may be removed such that the tip lumen includes an opening at its distal end. In other instances, openings may be located proximally of the distal end of the shunt tip between the distal end and the proximal end of the shunt tip. Such openings may preferably enter the tip lumen along a direction that is transverse to the longitudinal axis of the shunt tip.

Although it maybe preferred that the shunt tip include no openings when inserted into the eye of the patient, in some embodiments the shunt tip may include one or more openings before insertion into an eye, with additional openings being created after implantation to, e.g., increase fluid flow rates through the shunt tip.

The apparatus of the present invention may include shunt tips attached to the distal end of an existing tube in a known fluid shunting apparatus (such as those described herein). In such an embodiment, the shunt tip may preferably be provided separately from the apparatus, with the shunt tip attached over the distal end of the tube and retained in place thereon by, e.g., adhesives, a friction fit, welding, etc.

In other embodiments, the shunt tip may be formed integrally at the distal end of a tube in a one-piece, completely integral molded component that may be connected to diffusion chamber, etc. at the proximal end of the tube. In such an embodiment, the drainage openings may be formed (after implantation) at any selected location along the length of the tube (provided that the opening is located within the eye) and/or at the distal end of the tip.

FIG. 5 shows the use of the present invention in the form of a shunt tip alone, e.g. as a stand-alone fistula (or seton). Shunt tip 64 is placed directly into anterior chamber 60 and fluid flow is relieved by bleb 62. By forming one or more openings in the shunt tip after implantation, drainage may be more precisely controlled in the postoperative period (unlike traditional trabeculectomy surgery).

FIG. 6 shows a tube shunt tip configuration according to a preferred embodiment of the invention. Tube shunt assembly 70 is composed of shunt tip 72 affixed to tube shunt 76. Preferably, the point of fixation is an annular male to female mating at surface 74 that can be of any of a variety of conventional means. The tube and the shunt tip may be a one-piece completely integral unit or may be of separate bodies fitted together frictionally, adhesively, thermally, threadably connected or chemically welded to the tube. FIG. 6 shows a tube shunt having an outer diameter of 0.635 inches and tube tip having a first inner diameter of 0.305 inches that tapers along surface 78 to a point. These dimensions are not critical to the invention but only serve to show one preferred embodiment and its configuration using a male-female connection.

In determining preferred openings on the shunt tip, pressure and speed of flow is often calculated and compared to actual practice. Calculated pressure drop across the length of shunt assembly 70 is generally defined by Poiseuille's formula where μ=aqueous viscosity, I=length, Q=aqueous flow rate, $R_1$=radius on one side in metres, $R_2$=radius on another side in metres:

$$\text{Pressure Drop(mmHg)} = \frac{\mu l Q}{17\pi}\left[\frac{R_1^2 + R_1 R_2 + R_2^2}{3R_1^3 R_2^3}\right]$$

By using this calculation, one can make predictions on the actual pressure drop across a specific tube length and its best application to the desired outcome.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An implantable fluid shunting apparatus comprising:
   a tube comprising a proximal tube end, a distal tube end, and a tube lumen extending from the proximal tube end to the distal tube end;
   a shunt tip attached to the distal tube end, wherein a longitudinal axis extends between the distal tube end and a distal tip end, and wherein at least a portion of the shunt tip tapers when moving from the distal tube end towards the distal tip end of the shunt tip;
   a tip lumen extending through the shunt tip along the longitudinal axis, the tip lumen in fluid communication with the tube lumen, wherein at least a portion of the tip lumen is conically shaped when moving from the distal tube end towards the distal tip end, and wherein the tip lumen comprises a closed end proximate the distal end of the shunt tip;
   wherein the tip lumen is defined by a wall that comprises laser-ablatable material such that an opening can be formed through the wall and into the tip lumen using laser energy incident on an outer surface of the shunt tip.

2. An apparatus according to claim 1, wherein the shunt tip consists essentially of the laser-ablatable material.

3. An apparatus according to claim 1, wherein the proximal tube end is attached to an implantable diffusion chamber.

4. An apparatus according to claim 1, wherein the laser-ablatable material comprises polypropylene.

5. An apparatus according to claim 1, wherein the tube and the shunt tip comprise a one-piece completely integral unit.

6. An apparatus according to claim 1, wherein the shunt tip comprises a separate body fitted over the distal tube end.

7. An apparatus according to claim 6, wherein the shunt tip is frictionally attached to the tube.

8. An apparatus according to claim 6, wherein the shunt tip is adhesively attached to the tube.

9. An apparatus according to claim 6, wherein the shunt up is thermally or chemically welded to the tube.

10. An implantable fluid shunting apparatus comprising:
    a shunt tip comprising a proximal end and a distal end, wherein a longitudinal axis extends between the proximal end and the distal end, and wherein at least a portion of the shunt tip tapers when moving from the proximal end towards the distal end;
    a tip lumen extending through the shunt tip along the longitudinal axis, the tip lumen comprising an opening at the proximal end of the shunt tip, wherein the tip lumen is conically shaped when moving from the distal tube end towards the distal end, and wherein the tip lumen comprises a closed end proximate the distal end of the shunt tip;

wherein the tip lumen is defined by a wail that comprises laser-ablatable material such that an opening can be formed through the wall and into the tip lumen using laser energy incident on an outer surface of the shunt tip.

11. A method of providing an implantable shunt to drain fluid from an eye, the method comprising:

implanting a portion of a shunt apparatus within the eye of a subject, wherein the shunt apparatus comprises:

a tube comprising a proximal tube end, a distal tube end, and a tube lumen extending from the proximal tube end to the distal tube end;

a shunt tip attached to the distal tube end, wherein a longitudinal axis extends between the distal tube end and a distal tip end of the shunt tip, and wherein at least a portion of the shunt tip tapers when moving from the distal tube end towards the distal tip end;

a tip lumen that is conically shaped extending through the shunt tip along the longitudinal axis, the tip lumen in fluid communication with the tube lumen, wherein at least a portion of the tip lumen tapers when moving from the distal tube end towards the distal tip end, and wherein the tip lumen comprises a closed end proximate the distal end of the shunt tip;

forming an opening in the shunt tip after implanting the shunt tip in the eye, wherein fluid within the eye is capable of flowing through the tip lumen and into the tube lumen, wherein the opening is formed by ablating a portion of the shunt tip using laser energy.

12. A method according to claim 11, further comprising enlarging the opening after monitoring fluid flow through the tube lumen.

13. A method according to claim 11, wherein the laser energy is directed into the eye to form the opening.

14. A method according to claim 11, wherein the method further comprises forming two or more openings in the shunt tip after implanting the shunt tip in the eye.

* * * * *